(12) United States Patent
Fredriksson et al.

(10) Patent No.: US 10,850,125 B2
(45) Date of Patent: Dec. 1, 2020

(54) METHOD AND A CORRESPONDING RADIATION TREATMENT SYSTEM FOR GENERATING A RADIATION TREATMENT PLAN

(71) Applicant: RaySearch Laboratories AB, Stockholm (SE)

(72) Inventors: Albin Fredriksson, Stockholm (SE); Mats Holmström, Stockholm (SE); Kjell Eriksson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 16/731,346

(22) Filed: Dec. 31, 2019

(65) Prior Publication Data

US 2020/0215352 A1 Jul. 9, 2020

(30) Foreign Application Priority Data

Jan. 3, 2019 (EP) ...................................... 19150206

(51) Int. Cl.
*A61N 5/10* (2006.01)

(52) U.S. Cl.
CPC .................................. *A61N 5/1031* (2013.01)

(58) Field of Classification Search
CPC .............................. A61N 5/1031; A61N 5/103
See application file for complete search history.

(56) References Cited

U.S. PATENT DOCUMENTS 6,385,477 B1 * 5/2002 Werner .................. A61N 5/103
378/4

2015/0265851 A1 9/2015 Ma et al.
2017/0014642 A1 * 1/2017 An ........................ A61N 5/1043

FOREIGN PATENT DOCUMENTS

CN 107823806 A 3/2018
DE 698 26 277 T2 11/2005

OTHER PUBLICATIONS

Bernatowicz, Kinga et al., "Feasibility of online IMPT adaptation using fast, automatic and robust dose restoration," Phys. Med. Biol. 63 (2018), 13 pages.

* cited by examiner

*Primary Examiner* — Chih-Cheng Kao
(74) *Attorney, Agent, or Firm* — Faegre Drinker Biddle & Reath LLP

(57) ABSTRACT

The present disclosure generally relates to the field of radiation treatment. More specifically, the present disclosure generally relates to methods and radiation treatment systems for generating a radiation treatment plan. According to one example embodiment, a method may comprise dividing at least one dose characteristic related to a dose distribution for a ROI into a plurality of subintervals. The method may further comprise partitioning the ROI into a plurality of different partitions based on the subintervals. All voxels of the ROI with values within the same subinterval are partitioned into the same partition. For each of the plurality of different partitions, the method may comprise establishing a weight and specifying an optimization function for an obtainable dose distribution based on the respective subinterval of dose characteristics. The method may further comprise generating the radiation treatment plan based on said established weights and specified optimization functions.

15 Claims, 3 Drawing Sheets

US 10,850,125 B2

METHOD AND A CORRESPONDING RADIATION TREATMENT SYSTEM FOR GENERATING A RADIATION TREATMENT PLAN

This application claims the benefit of European Patent Application No. EP19150206.1, filed Jan. 3, 2019, the entire contents of which is incorporated by reference herein.

TECHNICAL FIELD

The present disclosure generally relates to the field of radiation treatment. More specifically, the present disclosure generally relates to methods and radiation treatment systems for generating a radiation treatment plan for radiation treatment. The present disclosure also relates to a computer program product and a computer readable medium

BACKGROUND

Radiation treatment may be used to treat tumorous tissue. In radiation treatment, a high energy beam of radiation is aimed towards a patient. More precisely, a radiation source produces a beam of radiation that is collimated and directed into a target volume in the patient. It is important that the radiation is delivered in such a way that the radiation to the malignant tissue, and to the surrounding tissue that should be protected, does not deviate too much from the clinical goals that are set. The dose and placement of the dose must be accurately controlled to ensure that the tumor receives sufficient radiation and such that damage to the surrounding healthy tissue is minimized.

The delivery of radiation treatment, e.g. for treatment of cancer, is typically a complicated process that requires both clinical and technical expertise in order to generate treatment plans that are safe and effective for the treatment. Treatment plans may be created and evaluated in a Treatment Planning System (TPS), hereinafter interchangeably referred to as radiation treatment system.

For the radiation treatment process, patients are imaged with, for example, Computed Tomography (CT) imaging and/or with other imaging techniques (e.g. MR, PET), depending on treatment site. Regions Of Interest (ROI), i.e. targets which are the locations the radiation is directed to, and normal tissue structures, i.e. the locations the radiation is minimized to, are delineated manually and/or semi-automatically or automatically on the acquired images. The clinical objectives of the treatment is specified, and an optimization algorithm is then used to generate the intensity and/or shape and/or modulation of radiation beams to achieve the treatment objectives. A dose distribution, a spatial representation of the dose the patient will receive, can then be calculated. The radiation treatment system is configured to determine or otherwise calculate the planned dose distribution in the ROI based on the acquired images.

SUMMARY

Although known strategies for determining radiation treatment plans often provide adequate treatment of tumorous tissue there is room for improvements. It is a desire to create even better radiation treatment plans, which find a set of treatment parameters which produce a dose distribution which mimics a desired dose distribution while balancing the trade-off between ensuring appropriate tumor coverage and avoiding excessive radiation to healthy structures. It is in view of the above considerations and others that the various aspects and embodiments disclosed herein have been made.

Despite the advances in radiation treatment technology, e.g. for cancer treatment, the present disclosure recognizes the fact that there is still an unmet need for radiation treatment systems and methods that provide improved radiation treatment plans which mimic a reference dose in a way that is more clinically relevant.

In view of the above, it is therefore a general object of the aspects and embodiments described throughout this disclosure to provide a solution, which overcomes one or more of the deficiencies noted hereinabove. More particularly, the various aspects and embodiments address the object of mimicking a reference dose with means to balance the tradeoff between being true to the original dose and giving leeway to the optimization.

The above-identified general object has been addressed by the appended independent claims. Advantageous embodiments are defined in the appended dependent claims.

According to a first aspect, there is provided a method of generating a radiation treatment plan for radiation treatment. The method comprises dividing at least one dose characteristic related to a dose distribution for a Region Of Interest (ROI) of a subject into a plurality of subintervals. Each subinterval has values of the at least one dose characteristic that differ from values of the at least one dose characteristic of other subintervals. The ROI of the subject is divided into a plurality of voxels. The method thereafter comprises partitioning the plurality of voxels into a plurality of different partitions based on the plurality of subintervals of the at least one dose characteristics. All voxels with values of the at least one dose characteristic that fall within the same subinterval are partitioned into the same partition. For each of the plurality of different partitions, the method further comprises establishing a weight. The weight reflects the relative importance of a dose criterion of the partition of the ROI of the subject. For each of the plurality of different partitions, the method further comprises specifying an optimization function for an obtainable dose distribution based on the respective subinterval of dose characteristics. Respective optimization function determines how the obtainable dose distribution is obtained in each partition. The method thereafter comprises generating the radiation treatment plan based on said established weights and said specified optimization functions for dose distribution for the respective partitions.

In some embodiments, the method further comprises obtaining a proposed dose distribution to be used in the radiation treatment plan for the subject. The proposed dose distribution specifies at least one desired dose level for the ROI of the subject.

In one embodiment, one of the at least one dose characteristic is a dose value received from the proposed dose distribution. The method then further comprises dividing the dose values of the proposed dose distribution into a plurality of subintervals. Each subinterval covers a part of the complete range of the absolute or relative value of the dose values ranging from 0 to a maximum dose. The maximum dose is a highest dose within the proposed dose distribution.

In one embodiment, the method further comprises specifying an optimization function for an obtainable dose distribution, for each of the plurality of different partitions, based on the respective dose values of the subintervals. The optimization function for each partition with dose values that are higher than a specified dose value is specified as a max and/or min reference Dose Value Histogram (DVH)

function. The optimization function for each partition with dose values that are lower than the specified dose value is specified as a max and/or min reference dose function.

In some embodiments, one of the at least one dose characteristic of the ROI of the subject is a probability distribution of the certainty that a dose level can be achieved. The method then further comprises dividing the probability distribution into a plurality of subintervals. The probability distribution may, for example, be divided into a plurality of subintervals, wherein each voxel of the ROI of the subject within a subinterval may have its own probability distribution. In one embodiment, the method further comprises establishing, for each of the plurality of different partitions, a weight that is higher for subintervals with a higher probability than the weight established for subintervals with a lower probability.

In one embodiment, the method further comprises specifying, for each of the plurality of different partitions, an optimization function for an obtainable dose distribution based on the respective probability values of the subintervals. The optimization function for a partition with a low probability aims for a same or equivalent dose distribution for a number of voxels as a corresponding number of voxels in the proposed dose distribution. The optimization function within a partition with a high probability aims for, for each voxel, a corresponding dose distribution as the respective voxel in the proposed dose distribution.

According to a second aspect, there is provided a radiation treatment system operative to perform the method according to the first aspect.

The radiation treatment system is configured to generate a radiation treatment plan for radiation treatment. The radiation treatment system comprises at least one processor and at least one memory. The at least one memory comprises instructions executable by the at least one processor whereby the radiation treatment system is operative to divide at least one dose characteristic related to a dose distribution for a ROI of a subject into a plurality of subintervals. Each subinterval has values of the at least one dose characteristic that differ from values of the at least one dose characteristic of other subintervals and the ROI of the subject is divided into a plurality of voxels. The radiation treatment system is further operative to partition the plurality of voxels into a plurality of different partitions based on the plurality of subintervals of the at least one dose characteristics. All voxels with values of the at least one dose characteristic that fall within the same subinterval are partitioned into the same partition. For each of the plurality of different partitions, the radiation treatment system is further operative to establish a weight. The weight reflects the relative importance of a dose criterion of the partition of the ROI of the subject. For each of the plurality of different partitions, the radiation treatment system is further operative to specify an optimization function for an obtainable dose distribution based on the respective subinterval of dose characteristics. Respective optimization function determines how the obtainable dose distribution is obtained in each partition. The radiation treatment system is thereafter operative to generate the radiation treatment plan based on said established weights and said specified optimization functions for dose distribution for the respective partitions.

In some embodiments, the at least one memory comprises instructions executable by the at least one processor whereby the radiation treatment system is operative to obtain a proposed dose distribution to be used in the radiation treatment plan for the subject. The proposed dose distribution specifies at least one desired dose level for the ROI of the subject.

In one embodiment, one of the at least one dose characteristic is a dose value received from the proposed dose distribution. The at least one memory comprises instructions executable by the at least one processor whereby the radiation treatment system is operative to divide the dose values of the proposed dose distribution into a plurality of subintervals. Each subinterval covers a part of the complete range of the absolute or relative dose values ranging from 0 to a maximum dose. The maximum dose is a highest dose within the proposed dose distribution.

In one embodiment, the at least one memory comprises instructions executable by the at least one processor whereby the radiation treatment system is operative to, for each of the plurality of different partitions, specify an optimization function for an obtainable dose distribution based on the respective dose values of the subintervals. The optimization functions for each partition with dose values that are higher than a specified dose value is specified as a max and/or min Dose Value Histogram (DVH) function. The optimization function for each partition with dose values that are lower than the specified dose value is specified as a max and/or min reference dose function.

In some embodiments, one of the at least one dose characteristic of the ROI of the subject is a probability distribution of the certainty that a dose level can be achieved. The at least one memory comprises instructions executable by the at least one processor whereby the radiation treatment system is operative to divide the probability distribution into a plurality of subintervals.

In one embodiment, the at least one memory comprises instructions executable by the at least one processor whereby the radiation treatment system is operative to, for each of the plurality of different partitions, establish a weight that is higher for subintervals with a higher probability than the weight established for subintervals with a lower probability.

In one embodiment, the at least one memory comprises instructions executable by the at least one processor whereby the radiation treatment system is operative to, for each of the plurality of different partitions, specify an optimization function for an obtainable dose distribution based on the respective probability values of the subintervals. The optimization function for a partition with a low probability aims for a same or equivalent dose distribution for a number of voxels as a corresponding numbers of voxels in the proposed dose distribution. The optimization function within a partition with a high probability aims for, for each voxel, a corresponding dose distribution as the respective voxel in the proposed dose distribution.

According to a third aspect, there is provided a computer program, comprising instructions which, when executed on a processing circuitry, cause the processing circuitry to carry out the method according to the first aspect.

According to a fourth aspect, there is provided a carrier containing the computer program of the third aspect, wherein the carrier is one of an electronic signal, optical signal, radio signal, or computer readable storage medium.

For example, a computer-readable medium may have stored thereon one or more sequences of instructions for causing one or more processors to dividing at least one dose characteristic related to a dose distribution for a ROI of a subject into a plurality of subintervals. Each subinterval has values of the at least one dose characteristic that differ from values of the at least one dose characteristic of other subintervals and the ROI of the subject is divided into a plurality of voxels. The computer-readable medium may further have stored thereon one or more sequences of instructions for causing one or more processors to partitioning the plurality of voxels into a plurality of different partitions based on the plurality of subintervals of the at least one dose characteristics. All voxels with values of the at least one dose characteristic that fall within the same subinterval are partitioned into the same partition. For each of the plurality of different partitions, the computer-readable medium may have stored thereon one or more sequences of instructions for causing one or more processors to establishing a weight. The weight reflects the relative importance of a dose criterion of the partition of the ROI of the subject. For each of the plurality of different partitions, the computer-readable medium may further have stored thereon one or more sequences of instructions for causing one or more processors to specifying an optimization function for an obtainable dose distribution based on the respective subinterval of dose characteristics. Respective optimization function determines how the obtainable dose distribution is obtained in each partition. The computer-readable medium may further have stored thereon one or more sequences of instructions for causing one or more processors to generating the radiation treatment plan based on said established weights and said specified optimization functions for dose distribution for the respective partitions.

Aspects and embodiments presented herein provide radiation treatment plans where a ROI is divided into a plurality of different partitions not only based on geometry and anatomy of the subject. The partitioning of the ROI into the plurality of different partitions according to the present disclosure is based on additional features relating to dose characteristics of the dose distribution. Due to this, the reference dose may be mimicked in a way that is more clinically relevant. Accordingly, it may be possible to mimic a reference dose with means to balance the tradeoff between being true to the original dose while giving leeway to the optimization. In other words, by the present disclosure it is made possible to improve the dose delivery to a subject without necessarily increasing the radiation dose. An additional possible advantage of this may be that the total radiation dose may be minimized, or at least reduced. A further additional possible advantage of this may be that automatic generating of radiation treatment plans may be enabled.

BRIEF DESCRIPTION OF DRAWINGS

These and other aspects, features and advantages will be apparent and elucidated from the following description of various embodiments, reference being made to the accompanying drawings, in which.

DETAILED DESCRIPTION

The present invention will now be described more fully hereinafter. The invention may, however, be embodied in many different forms and should not be construed as limited to the embodiments set forth herein. Rather, these embodiments are provided by way of example so that this disclosure will be thorough and complete, and will fully convey the scope of the invention to those persons skilled in the art. Like reference numbers refer to like elements or method steps throughout the description.

The aspects and embodiments disclosed herein relate to the generating of a radiation treatment plan for radiation treatment. The radiation treatment plan may be used for treating a treatment volume, i.e. a Region Of Interest (ROI) of a subject. The ROI of the subject may for example be treated in order to eliminate, or at least reduce, tumorous tissue, such as cancer.

Radiation treatment is often delivered to a subject, or a patient, in a number of sessions, also named fractions. The radiation delivered in each fraction can be the same as in other fractions, or the radiation can be different between the fractions. These fractions are generally created based on the anatomy or geometry of the subject. However, by generating the radiation treatment plan in an improved way, where the ROI of the subject is divided into partitions based on characteristics not only related to the geometry and anatomy of the ROI of the subject, a possible advantage of the disclosure herein may be that it is possible to improve the dose delivery to the ROI of the subject without having to increase the radiation.

In general, this disclosure therefore proposes a division of the ROI into a plurality of partitions in an improved way such that optimized treatment may be provided to a ROI of a subject in each partition.

Figure 1:
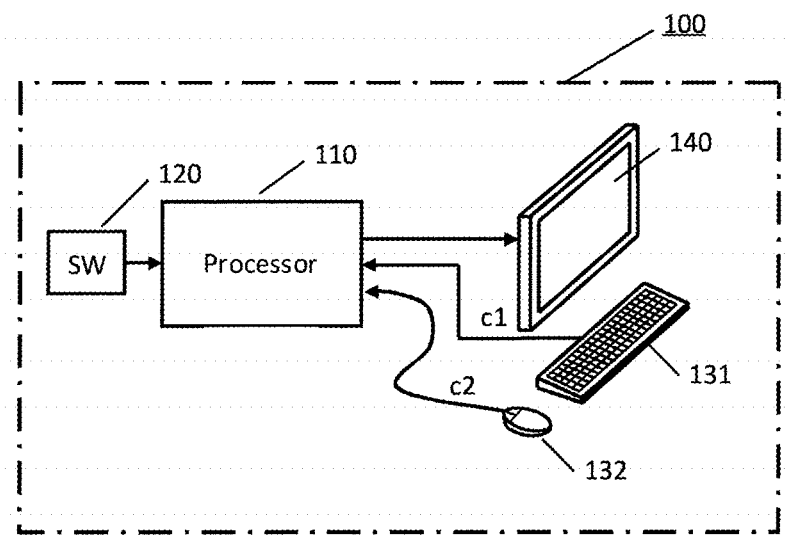
FIG. 1 schematically illustrates a radiation treatment system configured to generate a radiation treatment plan for radiation treatment.

Reference will now be made to the figures, where FIG. 1 illustrates an example of a radiation treatment system 100 where aspects and embodiments of the present invention may be applied. The radiation treatment system 100 is configured to generate a radiation treatment plan for radiation treatment. The radiation treatment plan may be used for treating a treatment volume, i.e. a region of interest (ROI) of a subject. The ROI generally comprises at least one target, typically represented by tumorous tissue and/or at least one Organ-At-Risk, (OAR), i.e. healthy tissue, where the amount of radiation shall be kept below certain levels, respectively. Additionally, the amount of radiation shall also be minimized and kept below certain levels for volumes external to the ROI.

With continued reference to FIG. 1, the radiation treatment system 100 comprises one or several processor(s) 110 or controller(s). The processor(s) 100 is/are communicatively connected to one or several memory/-ies 120. One or more of the memories 120 may comprise instructions executable by the processor(s) 110 whereby the radiation treatment system 100 is operative to perform the various functions and/or methods described throughout this disclosure.

The processor(s) 110 may also be communicatively connected to at least one user interface (UI) 131, 132, 140. A user or operator (not shown) may interact with and operate the UI 131, 132, 140, e.g., for controlling the operation of the radiation treatment system 100. To this end, the UI may thus comprise UI input device 131, 132 for receiving user input. The input device may be configured to receive commands c1 and c2 from the operator. The commands may specify criteria for generating the radiation treatment plan. The UI input devices illustrated in FIG. 1, are exemplified by a keyboard 131, for entering text, numbers and commands, and a mouse 132, for selecting and confirming selections. Additionally, or alternatively, the UI may comprise a UI output device 140 for outputting information to the user. Such information may, for example, be a description of the generated radiation treatment plan. In some embodiments, the UI 131, 132 and 140 may be implemented as a touch-sensitive UI. For example, the UI may comprise a touch-sensitive display suitably incorporating the functionalities of both a UI input device and a UI output device.

The memory/-ies 120 may comprise instructions executable by the processor(s) 110 whereby the radiation treatment system 100 is operative to generate a radiation treatment plan for radiation treatment. The radiation treatment plan may subsequently be used for treating a ROI of a subject. The radiation treatment plan may, for example, subsequently be used for treating cancer.

The memory/-ies 120 may comprise instructions executable by the processor(s) 110 whereby the radiation treatment system 100 is operative to divide at least one dose characteristic related to a dose distribution for a ROI of a subject into a plurality of subintervals. Each subinterval has values of the at least one dose characteristic that differ from values of the at least one dose characteristic of other subintervals. The ROI of the subject is divided into a plurality of voxels. The subintervals may be uniformly divided, i.e. may cover a number of equal intervals, or the subintervals may be unevenly divided, such that at least one interval may be larger than at least one other interval.

The at least one dose characteristic may be any characteristic that is related to the dose distribution for the ROI. An examples of such dose characteristic may be dose value. However, the dose characteristic is not limited to the dose per se, but can additionally, or alternatively, also be e.g. a probability distribution of a certainty that a dose level can be achieved.

In some embodiments, one dose characteristic related to the dose distribution for the ROI of the subject may be divided into a plurality of subintervals and the plurality of voxels of the ROI of the subject may be partitioned into a plurality of different partitions based on the plurality of subintervals of the dose characteristic. For example, in such embodiments, the ROI of the subject may be divided into a plurality of different partitions based on the dose value. In an alternative example, the ROI of the subject may be divided into a plurality of different partitions based on a probability distribution of a certainty that a dose level can be achieved.

In some embodiments, a plurality of dose characteristics related to the dose distribution may be used when the ROI of the subject may be partitioned into a plurality of different partitions. For example, in such embodiments, the ROI of the subject may be divided into a plurality of different partitions based on both the dose value and the probability distribution of a certainty that a dose level can be achieved.

Each subinterval may generally have values of the dose characteristic that differ from the other subintervals. However, in embodiments where there are more than one dose characteristics related to a dose distribution that are divided into subintervals, the values of each subinterval related to one of the dose characteristic may have values of the dose characteristic that differ from the other subintervals, while the values of the subintervals of the other dose characteristics may be overlapping.

The memory/-ies 120 may further comprise instructions executable by the processor(s) 110 whereby the radiation treatment system 100 is operative to partition the plurality of voxels into a plurality of different partitions based on the plurality of subintervals of the at least one dose characteristics. All voxels with values of the at least one dose characteristic that fall within the same subinterval are partitioned into the same partition.

For each of the plurality of different partitions, the radiation treatment system 100 is operative to establish a weight. The weight reflects the relative importance of a dose criterion of the partition of the ROI of the subject. In one exemplary embodiment, a high weight may be established for partitions where it is a high certainty of which dose to obtain.

For each of the plurality of different partitions, the radiation treatment system 100 is further operative to specify an optimization function for an obtainable dose distribution based on the respective subinterval of dose characteristics. The respective optimization function determines how the obtainable dose distribution is obtained in each partition. The optimization function may, for example, be a constraint, an objective function, or a constituent of the objective function. Accordingly, the respective optimization function determines what is important when the obtainable dose distribution is obtained, or, expressed in other words, how the quality of the dose distribution should be measured. The optimization function may determine which type of penalty that should be selected for each partition. Non-limiting examples of optimization functions that may be used are max reference dose functions, min/max reference Dose Value Histogram (DVH) functions, min/max Equivalent Uniform Dose (EUD) functions, min/max reference dose functions and uniform reference dose functions.

The radiation treatment system 100 is thereafter operative to generate the radiation treatment plan based on said established weights and said specified optimization functions for dose distribution for the respective partitions.

By the proposed radiation treatment system 100, it may be possible to specify the requirements for each partition based on the subinterval for the at least one dose characteristic and it may accordingly be possible to meet requirements on a per voxel level if wanted. The generated radiation treatment plan may be enabled to stay true to the original dose distribution in a more precise way than previous systems, as the ROI is divided into partitions in a way that not only considering the anatomy of the subject. Each of the plurality of different partitions may receive different weights and optimization functions based on the respective subinterval of dose characteristics such that the radiation treatment plan may be optimized for each partition. Accordingly, the proposed radiation treatment system 100 may additionally provide more leeway to the optimization and may chose a more suitable optimization function for each of the different partitions. Due to this, the reference dose may be mimicked in a way that is more clinically relevant. In other words, by the present disclosure it is made possible to improve the dose delivery to a subject without necessarily increasing the radiation dose. An additional possible advantage of this may be that the total radiation dose may be minimized, or at least reduced.

In one embodiment, the same optimization function for an obtainable dose distribution may be specified for a plurality of the different partitions. However, the established weights for the plurality of the different partitions may still differ between the plurality of different partitions. This may be advantageous when it is equally important how the quality of the dose distribution should be measured for the plurality of different partitions, but the relative importance of a dose criterion of the partition of the ROI of the subject may differ between the pluralities of different partitions. In one embodiment, the at least one memory may comprise instructions executable by the at least one processor 110 whereby the radiation treatment system 100 is operative to obtain a proposed dose distribution to be used in the radiation treatment plan for the subject. The proposed dose distribution may specify at least one desired dose level for the ROI of the subject. The obtained proposed dose distribution to be used in the generation of the radiation treatment plan for the subject may, for example, have been predicted by machine learning, been received from a previous plan, i.e. fallback, or may have been received from a multi-criteria optimization (MCO), e.g., using Pareto surface navigation.

In some embodiments, one of the at least one dose characteristic may be a dose value received from the proposed dose distribution. The at least one memory 120 may then comprise instructions executable by the at least one processor 110 whereby the radiation treatment system may be operative to divide the dose values of the proposed dose distribution into a plurality of subintervals. Each subinterval may cover a part of the complete range of the absolute or relative dose values ranging from 0 to a maximum dose. The maximum dose may be a highest dose within the proposed dose distribution. Alternatively, there may be a subinterval which covers all dose values above a certain dose value. This subinterval may then be the last subinterval and may only have a lower limit, but not a higher limit. This subinterval may additionally, or alternatively also cover dose values above the maximum dose. The subintervals may, for example, be divided into subintervals based on a fixed number of Gy or based on a fixed number of subintervals within the proposed dose distribution. Alternatively, the subintervals may be divided into subintervals based on percentages of the prescribed dose.

According to one example, all dose values of the complete range of the absolute or relative dose values fall within a subinterval and may hence be covered by a subinterval. According to another example, some of the dose values of the complete range of the absolute or relative dose values are not covered by a subinterval.

When one of the at least one dose characteristic is a dose value received from the proposed dose distribution, the weight for each partition may, according to one embodiment, be established based on the distance from the target. A high weight may, for example, be established for partitions that have subintervals of the at least one dose characteristics with values that relate to the target and subintervals with low dose values. In these partitions there is a high certainty of which dose to obtain.

In one embodiment, when one of the at least one dose characteristic may be a dose value received from the proposed dose distribution, the at least one memory 120 may comprise instructions executable by the at least one processor 110 whereby the radiation treatment system 100 is operative to, for each of the plurality of different partitions, specify an optimization function for an obtainable dose distribution based on the respective dose values of the subintervals. The optimization functions for each partition with dose values that are higher than a specified dose value may be specified as a min/max reference Dose Value Histogram (DVH) function. A max and/or min reference DVH function is a optimization function that may penalize parts of the cumulative DVH of the obtainable dose distribution in the considered partition that may exceed or go below the cumulate DVH of the proposed dose distribution in the considered partition. The optimization function for each partition with dose values that are lower than the specified dose value may be specified as a min and/or max reference dose function. A max and/or min reference dose function is a optimization function that may penalize voxels with obtainable dose values that exceed or go below the corresponding proposed voxel dose values in the considered partition. Accordingly, it may be possible to keep the spatial distribution of dose in low dose regions, whereas more leeway may be given to high dose regions. In some embodiments, one of the at least one dose characteristic of the ROI of the subject may be a probability distribution of the certainty that a dose level can be achieved. The at least one memory 120 may comprise instructions executable by the at least one processor 110 whereby the radiation treatment system 100 may be operative to divide the probability distribution into a plurality of subintervals. Accordingly, the subintervals may, for example, be divided into a subinterval where a dose level can be achieved with a very high probability, a subinterval where it is very uncertain whether a dose level can be achieved, i.e. that a dose level can be achieved has a low probability, and subintervals therein between. A subinterval may, for example, comprise a single probability value, or a plurality of values, e.g. a range of values.

The probability distribution of the certainty that a dose level can be achieved may, for example, be obtained from a machine learning algorithm. The machine learning algorithm may provide a probability for each dose level interval per voxel. Based on this a probability distribution of the certainty that a dose level can be achieved in each voxel may be created. In one embodiment, the radiation treatment system 100 may be operative to, for each of the plurality of different partitions, establish a weight that is higher for subintervals with a higher probability than the weight established for subintervals with a lower probability.

As previously described, a plurality of voxels of a ROI of a subject may be divided into a plurality of partitions based on a plurality of dose characteristics related to the dose distribution for the ROI of the subject. In one exemplary embodiment, the radiation treatment system 100 may be operative to divide the probability distribution into a plurality of subintervals, wherein each voxel within a subinterval may have its own probability distribution. The voxels own probability distributions may then be used in the mimicking of the reference dose. For example, if the probability for a voxel may be scattered, the weight for that voxel may be established to zero.

When one of the at least one dose characteristic of the ROI of the subject may be a probability distribution of the certainty that a dose level can be achieved, the radiation treatment system 100 may be operative to, for each of the plurality of different partitions, specify an optimization function for an obtainable dose distribution based on the respective probability values of the subintervals. The optimization function for a partition with a low probability may aim for a same, or equivalent, dose distribution for a number of voxels as a corresponding number of voxels in the proposed dose distribution. Their order may be neglected. Accordingly, in partitions where the probability is low to achieve a dose level, i.e. the uncertainty is high, the aim is to achieve the same dose distribution for approximately the same number of voxels as in the proposed dose distribution, but without regarding the geometric position. This means that the aim is to achieve the same, or equivalent, dose distribution as in the proposed dose distribution for the same, or equivalent number of voxels, but it does not necessarily mean that it is the corresponding voxels as in the proposed dose distribution that achieve the same dose distribution. This means that a same or equivalent DVH is achieved. The optimization function within a partition with a high probability aims for, for each voxel, a corresponding dose as the respective voxel in the proposed dose distribution. Accordingly, in partitions where the probability is high, the aim is that each voxel in the obtainable dose distribution should have a corresponding dose as the respective voxel in the proposed dose distribution. Hence, the proposed radiation treatment system provides an improved radiation treatment plan where the optimization functions may be specified based on the respective subinterval of the probability distribution of the certainty that a dose level can be achieved, and the radiation treatment plan may be adapted with regard to the different values of each subinterval.

Despite the advances in radiation treatment technology, e.g. for cancer treatment, the present disclosure recognizes the fact that there is still an unmet need for radiation treatment systems and methods that provide improved radiation treatment plans for radiation treatment which enable mimicking of a reference dose in a way that is more clinically relevant.

As described earlier herein and despite the advances in radiation treatment technology, existing radiation treatment plans are generally not generated with regards to different characteristics of different partitions of a ROI of a subject other than possibly the geometry of the ROI of the subject. To address the still unmet need of improved radiation treatment plans for radiation treatment which enable mimicking of a reference dose in a way that is more clinically relevant, which also enables automatic generating of radiation treatment plans, and in accordance with an aspect, the present disclosure therefore also proposes a method as is schematically illustrated in the flow chart in FIG. 2.

Figure 2:
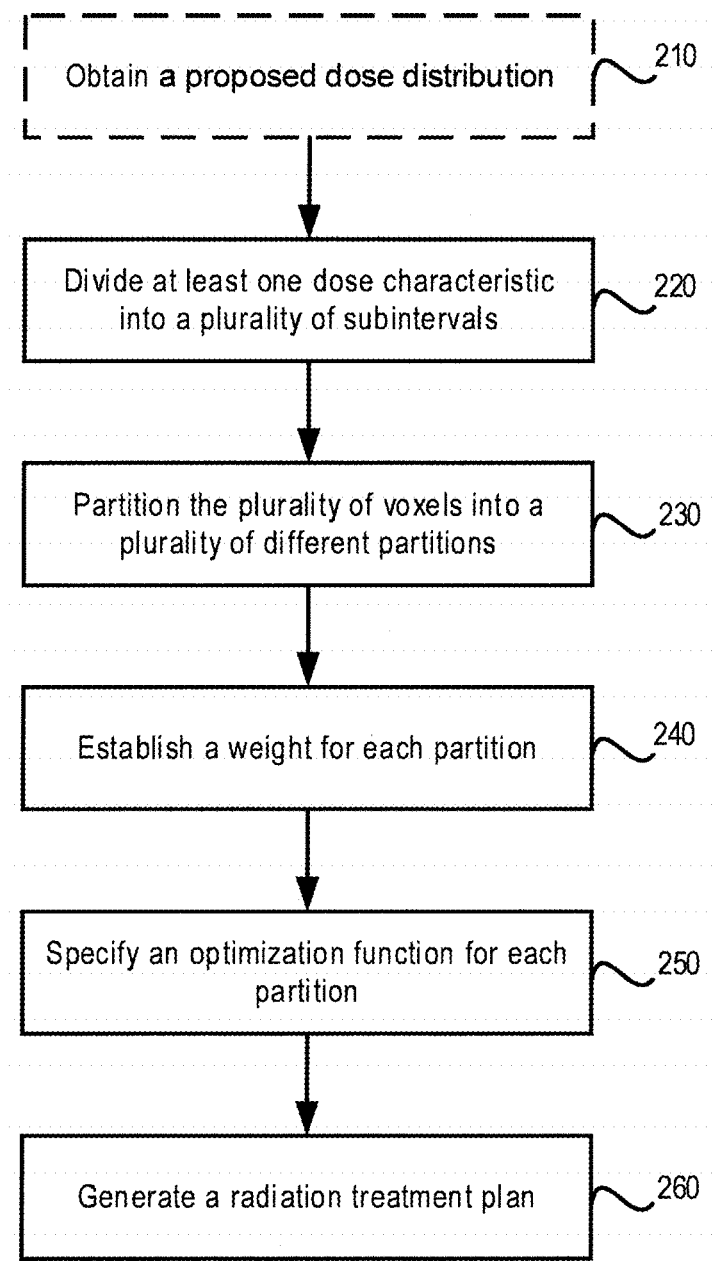
FIG. 2 schematically illustrates a flow chart of a method performed by, or implemented in, a radiation treatment system.

Accordingly, FIG. 2 schematically illustrates a flow chart of a method 200 of generating a radiation treatment plan for radiation treatment.

The method 200 is advantageously, but not necessarily, performed by or otherwise implemented in the radiation treatment system 100 shown in FIG. 1.

Action 210: Optionally, the method may start with that a proposed dose distribution to be used in the creation of a radiation treatment plan for a subject may be obtained. Said proposed dose distribution may specify at least one desired dose level for a ROI of the subject.

Action 220: At least one dose characteristic related to a dose distribution for the ROI of the subject is divided into a plurality of subintervals. Each subinterval has values of the at least one dose characteristic that differ from values of the at least one dose characteristic of other subintervals. The ROI of the subject is divided into a plurality of voxels. In one embodiment, one of the at least one dose characteristic may, for example, be a dose value received from the proposed dose distribution. Then, the dose values of the proposed dose distribution may be divided into a plurality of subintervals. Each subinterval may cover a part of the complete range of the absolute or relative value of the dose values ranging from 0 to a maximum dose. The maximum dose may be a highest dose within the proposed dose distribution. Additionally, or alternatively, one of the at least one dose characteristic may, for example, be a probability distribution of the certainty that a dose level can be achieved. Then, the probability distribution may be divided into a plurality of subintervals.

Action 230: The plurality of voxels are partitioned into a plurality of different partitions based on the plurality of subintervals of the at least one dose characteristics. All voxels with values of the at least one dose characteristic that fall within the same subinterval are partitioned into the same partition.

Action 240: For each of the plurality of different partitions, a weight is established. The weight reflects the relative importance of a dose criterion of the partition of the ROI of the subject. In one embodiment, when one of the at least one dose characteristics is a probability distribution of the certainty that a dose level can be achieved, for each of the plurality of different partitions, a weight may be established that is higher for subintervals with a higher probability than the weight established for subintervals with a lower probability.

Action 250: For each of the plurality of different partitions, an optimization function for an obtainable dose distribution is specified based on the respective subinterval of dose characteristics. The respective optimization function may, for example, be a constraint, an objective function, or a constituent of the objective function and determines how the obtainable dose distribution is obtained in each partition. The respective optimization function determines how the quality of the dose distribution is measured.

In one embodiment, when one of the at least one dose characteristics is a dose value, an optimization function for an obtainable dose distribution may be specified for each of the plurality of different partitions based on the respective dose values of the subintervals. The optimization functions for partitions with dose values that are higher than a specified dose value may be specified as a DVH function and the optimization function for partitions with dose values that are lower than the specified dose value may be specified as a max reference dose function.

In one embodiment, when one of the at least one dose characteristics is a probability distribution of the certainty that a dose level can be achieved, an optimization function for an obtainable dose distribution may be specified based on the respective probability values of the subintervals. The optimization function for a partition with a low probability may aim for a same or equivalent dose distribution for a number of voxels as a corresponding number of voxels in the proposed dose distribution and the optimization function within a partition with a high probability may aim for, for each voxel, a corresponding dose distribution as the respective voxel in the proposed dose distribution.

Action 260: Thereafter, the radiation treatment plan is generated based on said established weights and said specified optimization functions for dose distribution for the respective partitions.

As will be appreciated from the discussion above, the present disclosure proposes a way of partitioning a ROI of a subject in order to generate a more precise radiation treatment plan. The generation of the radiation treatment plan uses at least one dose characteristic related to a dose distribution in order to partitioning the ROI of the subject. Accordingly, it may be possible to specify the requirements for each partition based on the subinterval for the at least one dose characteristic and it may accordingly be possible to meet requirements on a per voxel level if wanted. The generated radiation treatment plan may be enabled to stay true to the original in a more precise way than previous systems, as the ROI is divided into partitions in a way that not only considering the anatomy of the subject. Additionally, the method may provide more leeway to the optimization. Hence, a more suitable optimization function for each of the different partitions may be chosen. Improved radiation treatment plans in turn may lead to improved cancer treatment.

Figure 3:
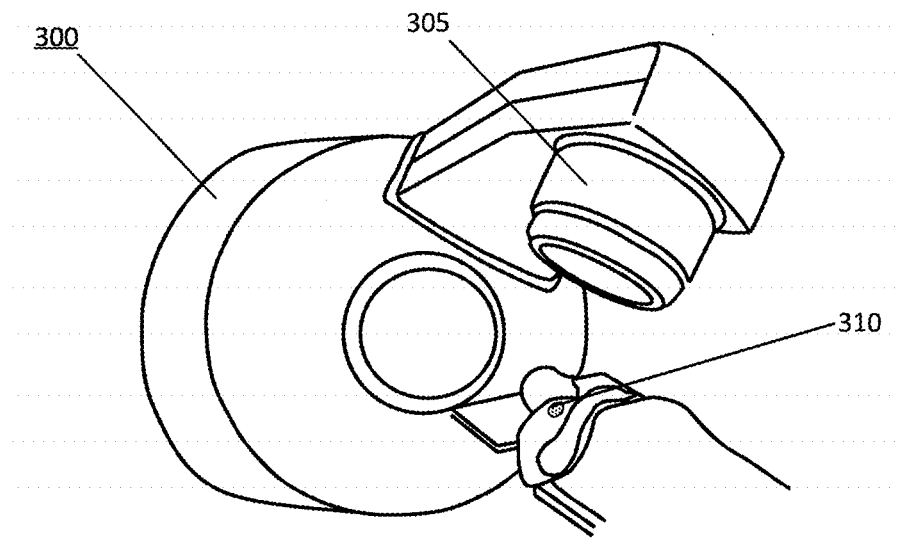
FIG. 3 schematically illustrates a radiation therapy machine.

FIG. 3 schematically illustrates a radiation therapy machine 300 according in which the generated radiation treatment plan may be used. The radiation therapy machine 300 is configured to receive the radiation treatment plan determined by the radiation treatment system 100. The radiation therapy machine 300 is further configured to carry out therapy in respect of the treatment volume 310 in a patient's body by controlling at least one radiation source 305 of the machine 300 in accordance with the generated radiation treatment plan. Thus, the at least one radiation source 305 may for example be configured to emit radiation towards the treatment volume 310 in the form of photons, electrons, protons, carbon ions, helium ions, or other ions.

Figure 4:
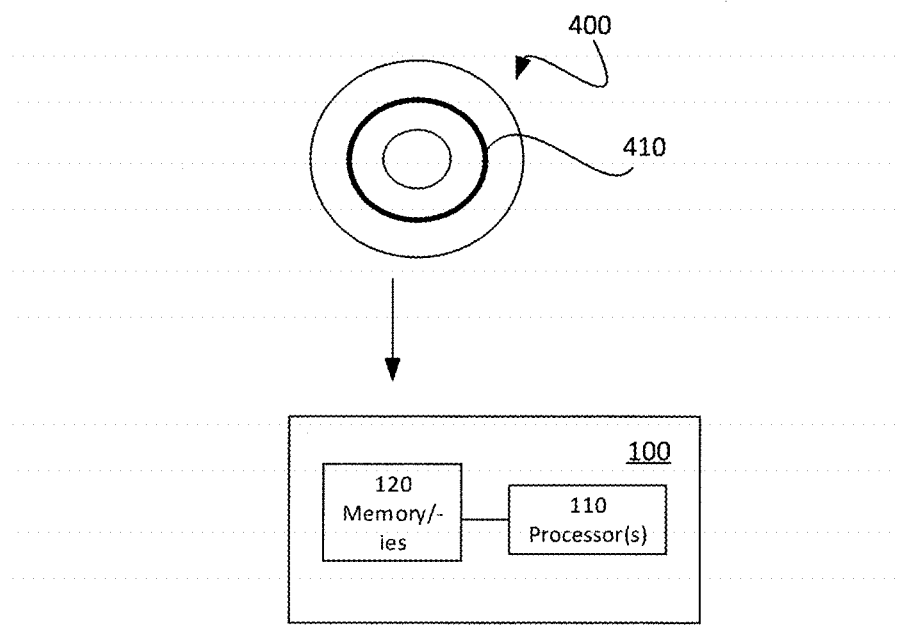
FIG. 4 schematically illustrates a carrier containing a computer program, in accordance with one aspect.

Turning now to FIG. 4, another aspect will be briefly discussed. FIG. 4 shows an example of a computer-readable medium, in this example in the form of a data disc 400. In one embodiment the data disc 400 is a magnetic data storage disc. The data disc 400 is configured to carry instructions 410 that can be loaded into a memory 120 of a radiation treatment system, such as the radiation treatment system 100 illustrated in FIG. 1. Upon execution of said instructions by a processor 110 of the system 100, the radiation treatment system 100 is caused to execute a method or procedure according to any one of the methods disclosed in this disclosure, for example in conjunction with FIG. 2. The data disc 400 is arranged to be connected to or within and read by a reading device (not shown), for loading the instructions into the processor 110. One such example of a reading device in combination with one (or several) data disc(s) 400 is a hard drive. It should be noted that the computer-readable medium can also be other mediums such as compact discs, digital video discs, flash memories or other memory technologies commonly used. In such an embodiment the data disc 400 is one type of a tangible computer-readable medium. The instructions may alternatively be downloaded to a computer data reading device, such as a computer or other system capable of reading computer coded data on a computer-readable medium, by comprising the instructions in a computer-readable signal (not shown) which is transmitted via a wireless (or wired) interface (for example via the Internet) to the computer data reading device for loading the instructions into a processor 110 of the radiation treatment system 100. In such an embodiment, the computer-readable signal is one type of a non-tangible computer-readable medium.

In the detailed description hereinabove, for purposes of explanation and not limitation, specific details are set forth in order to provide a thorough understanding of various aspects and embodiments described in this disclosure. In some instances, detailed descriptions of well-known devices, components, circuits, and methods have been omitted so as not to obscure the description of the embodiments disclosed herein with unnecessary detail. All statements herein reciting principles, aspects, and embodiments disclosed herein, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure. Thus, for example, it will be appreciated that block diagrams herein can represent conceptual views of illustrative circuitry or other functional units embodying the principles of the described embodiments. Similarly, it will be appreciated that any flow charts and the like represent various processes which may be substantially represented in computer readable medium and so executed by a computer or processor, whether or not such computer or processor is explicitly shown. The functions of the various elements including functional blocks, may be provided through the use of hardware such as circuit hardware and/or hardware capable of executing software in the form of coded instructions stored on the above-mentioned computer readable medium. Thus, such functions and illustrated functional blocks are to be understood as being either hardware-implemented and/or computer-implemented, and thus machine-implemented. In terms of hardware implementation, the functional blocks may include or encompass, without limitation, digital signal processor (DSP) hardware, reduced instruction set processor, hardware (e.g., digital or analog) circuitry including but not limited to application specific integrated circuit(s) [ASIC], and/or field programmable gate array(s) (FPGA(s)), and (where appropriate) state machines capable of performing such functions. In terms of computer implementation, a computer is generally understood to comprise one or more processors or one or more controllers. When provided by a computer or processor or controller, the functions may be provided by a single dedicated computer or processor or controller, by a single shared computer or processor or controller, or by a plurality of individual computers or processors or controllers, some of which may be shared or distributed. Moreover, use of the term "processor" or "controller" may also be construed to refer to other hardware capable of performing such functions and/or executing software, such as the example hardware recited above.

Modifications and other variants of the described embodiments will come to mind to one skilled in the art having benefit of the teachings presented in the foregoing description and associated drawings. Therefore, it is to be understood that the embodiments are not limited to the specific example embodiments described in this disclosure and that modifications and other variants are intended to be included within the scope of this disclosure. Furthermore, although specific terms may be employed herein, they are used in a generic and descriptive sense only and not for purposes of limitation. Therefore, a person skilled in the art would recognize numerous variations to the described embodiments that would still fall within the scope of the appended claims. As used herein, the terms "comprise/comprises" or "include/includes" do not exclude the presence of other elements or steps. Furthermore, although individual features may be included in different claims, these may possibly advantageously be combined, and the inclusion of different claims does not imply that a combination of features is not feasible and/or advantageous. In addition, singular references do not exclude a plurality.

The invention claimed is:

1. A method of generating a radiation treatment plan for radiation treatment, the method comprising:
   dividing at least one dose characteristic related to a dose distribution for a Region Of Interest (ROI) of a subject into a plurality of subintervals, wherein each subinterval has values of the at least one dose characteristic that differ from values of the at least one dose characteristic of other subintervals and wherein said ROI of the subject is divided into a plurality of voxels;
   partitioning the plurality of voxels into a plurality of different partitions based on the plurality of subintervals of the at least one dose characteristic, wherein all voxels with values of the at least one dose characteristic that fall within the same subinterval are partitioned into the same partition;
   for each of the plurality of different partitions, establishing a weight, wherein the weight reflects the relative importance of a dose criterion of the partition of the ROI of the subject;

for each of the plurality of different partitions, specifying an optimization function for an obtainable dose distribution based on the respective subinterval of dose characteristics, wherein a respective optimization function determines how the obtainable dose distribution is obtained in each partition; and generating the radiation treatment plan based on said established weights and said specified optimization functions for dose distribution for the respective partitions, the radiation treatment plan configured to control a radiation therapy machine to carry out therapy in respect of the ROI of the subject.

2. The method according to claim 1, wherein the method further comprises:

obtaining a proposed dose distribution to be used in the radiation treatment plan for the subject, wherein said proposed dose distribution specifies at least one desired dose level for the ROI of the subject.

3. The method according to claim 2, wherein one of the at least one dose characteristic is a dose value received from the proposed dose distribution, the method comprises:

dividing the dose values of the proposed dose distribution into a plurality of subintervals, wherein each subinterval covers a part of the complete range of the absolute or relative value of the dose values ranging from 0 to a maximum dose and wherein the maximum dose is a highest dose within the proposed dose distribution.

4. The method according to claim 3, wherein the method further comprises:

for each of the plurality of different partitions, specifying an optimization function for an obtainable dose distribution based on the respective dose values of the subintervals, wherein the optimization functions for partitions with dose values that are higher than a specified dose value are specified as a max and/or min Dose Value Histogram (DVH) function and the optimization function for partitions with dose values that are lower than the specified dose value are specified as a max and/or min reference dose function.

5. The method according to claim 1, wherein one of the at least one dose characteristic of the ROI of the subject is a probability distribution of the certainty that a dose level can be achieved and wherein the method comprises:

dividing the probability distribution into a plurality of subintervals.

6. The method according to claim 5, wherein the method further comprises:

for each of the plurality of different partitions, establishing a weight that is higher for subintervals with a higher probability than the weight established for subintervals with a lower probability.

7. The method according to claim 5, wherein the method further comprises:

for each of the plurality of different partitions, specifying an optimization function for an obtainable dose distribution based on the respective probability values of the subintervals, wherein the optimization function for a partition with a low probability aims for a same or equivalent dose distribution for a number of voxels as a corresponding number of voxels in a proposed dose distribution, and wherein the optimization function within a partition with a high probability aims for, for each voxel, a corresponding dose distribution as the respective voxel in the proposed dose distribution.

8. A non-transitory computer-readable medium encoded with a computer program, comprising instructions which, when executed on a processor, cause the processor to carry out the method according to claim 1.

9. A radiation treatment system configured to generate a radiation treatment plan for radiation treatment, the radiation treatment system comprising:

at least one processor; and at least one memory comprising instructions executable by the at least one processor whereby the radiation treatment system is operative to:

divide at least one dose characteristic related to a dose distribution for a Region Of Interest (ROI) of a subject into a plurality of subintervals, wherein each subinterval has values of the at least one dose characteristic that differ from values of the at least one dose characteristic of other subintervals and wherein said ROI of the subject is divided into a plurality of voxels;

partition the plurality of voxels into a plurality of different partitions based on the plurality of subintervals of the at least one dose characteristic, wherein all voxels with values of the at least one dose characteristic that fall within the same subinterval are partitioned into the same partition;

for each of the plurality of different partitions, establish a weight, wherein the weight reflects the relative importance of a dose criterion of the partition of the ROI of the subject;

for each of the plurality of different partitions, specify an optimization function for an obtainable dose distribution based on the respective subinterval of dose characteristics, wherein a respective optimization function determines how the obtainable dose distribution is obtained in each partition; and generate the radiation treatment plan based on said established weights and said specified optimization functions for dose distribution for the respective partitions, the radiation treatment plan configured to control a radiation therapy machine to carry out therapy in respect of the ROI of the subject.

10. The radiation treatment system according to claim 9, wherein the at least one memory comprises instructions executable by the at least one processor whereby the radiation treatment system is operative to:

obtain a proposed dose distribution to be used in the radiation treatment plan for the subject, wherein said proposed dose distribution specifies at least one desired dose level for the ROI of the subject.

11. The radiation treatment system according to claim 10, wherein one of the at least one dose characteristic is a dose value received from the proposed dose distribution and wherein the at least one memory comprises instructions executable by the at least one processor whereby the radiation treatment system is operative to:

divide the dose values of the proposed dose distribution into a plurality of subintervals, wherein each subinterval covers a part of the complete range of the absolute or relative dose values ranging from 0 to a maximum dose and wherein the maximum dose is a highest dose within the proposed dose distribution.

12. The radiation treatment system according to claim 11, wherein the at least one memory comprises instructions executable by the at least one processor whereby the radiation treatment system is operative to:

for each of the plurality of different partitions, specify an optimization function for an obtainable dose distribution based on the respective dose values of the subintervals, wherein the optimization functions for partitions with dose values that are higher than a specified dose value are specified as a max and/or min Dose Value Histogram (DVH) function and the optimization function for partitions with dose values that are lower than the specified dose value are specified as a max and/or min reference dose function.

13. The radiation treatment system according to claim 9, wherein one of the at least one dose characteristic of the ROI of the subject is a probability distribution of the certainty that a dose level can be achieved and wherein the at least one memory comprises instructions executable by the at least one processor whereby the radiation treatment system is operative to:

divide the probability distribution into a plurality of subintervals.

14. The radiation treatment system according to claim 13, wherein the at least one memory comprises instructions executable by the at least one processor whereby the radiation treatment system is operative to:

for each of the plurality of different partitions, establish a weight that is higher for subintervals with a higher probability than the weight established for subintervals with a lower probability.

15. The radiation treatment system according to claim 13, wherein the at least one memory comprises instructions executable by the at least one processor whereby the radiation treatment system is operative to:

for each of the plurality of different partitions, specify an optimization function for an obtainable dose distribution based on the respective probability values of the subintervals, wherein the optimization function for a partition with a low probability aims for a same or equivalent dose distribution for a number of voxels as a corresponding number of voxels in a proposed dose distribution, and wherein the optimization function within a partition with a high probability aims for, for each voxel, a corresponding dose distribution as the respective voxel in the proposed dose distribution.

* * * * *